US011344246B2

(12) United States Patent
Hajimolahoseini et al.

(10) Patent No.: US 11,344,246 B2
(45) Date of Patent: May 31, 2022

(54) LONG QT SYNDROME DIAGNOSIS AND CLASSIFICATION

(71) Applicants: QUEEN'S UNIVERSITY AT KINGSTON, Kingston (CA); KINGSTON HEALTH SCIENCES CENTRE, Kingston (CA)

(72) Inventors: Habib Hajimolahoseini, Montreal (CA); Damian P. Redfearn, Kingston (CA); Javad Hashemi, Kingston (CA)

(73) Assignees: Queen's University at Kingston, Kingston (CA); Kingston Health Sciences Centre, Kingston (CA)

( * ) Notice: Subject to any disclaimer, the term of this patent is extended or adjusted under 35 U.S.C. 154(b) by 199 days.

(21) Appl. No.: 16/715,017

(22) Filed: Dec. 16, 2019

(65) Prior Publication Data

US 2020/0196898 A1    Jun. 25, 2020

Related U.S. Application Data

(60) Provisional application No. 62/782,738, filed on Dec. 20, 2018.

(51) Int. Cl.
*A61B 5/364* (2021.01)
*A61B 5/36* (2021.01)
*A61B 5/00* (2006.01)

(52) U.S. Cl.
CPC ............. *A61B 5/364* (2021.01); *A61B 5/36* (2021.01); *A61B 5/7239* (2013.01)

(58) Field of Classification Search
None
See application file for complete search history.

(56) References Cited

U.S. PATENT DOCUMENTS

| 7,623,910 B2 * | 11/2009 | Couderc ................ A61B 5/349 600/509 |
| 2007/0260151 A1 * | 11/2007 | Clifford ............... A61B 5/7264 600/509 |
| 2008/0015453 A1 * | 1/2008 | Lux ........................ A61B 5/349 600/509 |
| 2018/0116593 A1 * | 5/2018 | An ........................ A61N 1/0587 |
| 2021/0275080 A1 * | 9/2021 | Noseworthy .......... A61B 5/339 |

OTHER PUBLICATIONS

Waddell-Smith, K. et al., "How to measure a QT interval", Medical Journal of Australia, vol. 207 (3), pp. 107-110, (2017).

(Continued)

*Primary Examiner* — Kennedy Schaetzle
(74) *Attorney, Agent, or Firm* — Stephen J. Scribner

(57) ABSTRACT

A method for detecting long QT syndrome in a subject comprises obtaining data corresponding to an electrocardiogram (ECG) signal of the subject, identifying a set of features in the data based on selected inflection points of the ECG signal, using the set of features to categorize segments of the ECG signal, and using the categorized segments of the ECG signal and the inflection points to classify the ECG signal as normal or as long QT syndrome. Long QT syndrome is detected when the subject's ECG signal is classified as long QT syndrome. The method may include determining whether the long QT syndrome is Type 1 or Type 2.

17 Claims, 8 Drawing Sheets

(56) References Cited

OTHER PUBLICATIONS

Immnanuel, S. et al., "T-wave morphology can distinguish healthy controls from LQTS patients" Physiological Measurement, vol. 37, No. 9, pp. 1456-1473, (2016).
Hughes, N.P., et al., "Markov Models for Automated ECG Interval Analysis" Advances in Neural Information Processing Systems, pp. 611-618, (2004).
Martinez, J.P., et al., "Methodological Principles of T Wave Alternans Analysis: A Unified Framework", IEEE Transactions on Biomedical Engineering, vol. 52, No. 4, pp. 599-613, (2005).
Jane, R. et al., "Evaluation of an Automatic Threshold Based Detector of Waveform Limits in Holter ECG with the QT Database" Computers in Cardiology IEEE, vol. 24, pp. 295-299, (1997).
Struijk, J.J. et al., "Classification of the long-QT syndrome based on discriminant analysis of T-wave morphology" Medical and Biological Engineering and Computing, vol. 44. No 7, pp. 543-549, (2006).
Marsanova, L. et al., "ECG features and methods for automatic classification of ventricular premature and ischemic heartbeats: A comprehensive experimental study" Scientific Reports, vol. 7, No. 1, p. 11239, (2017).
Thorpe, J.R. et al., "Comparative Study of T-amplitude Features for Fitness Monitoring Using the ePatch ® ECG Recorder" Engineering in Medicine and Biology Society (EMBC), 36th Annual International Confererce of the IEEE, pp. 4172-4175, (2014).
Goutas, A. el al., "Digital fractional order differentiation-based algorithm for P and T-waves detection and delineation" ITBM-RBM, vol. 26, No. 2, pp. 127-132, (2005).
Singh, Y.N., "ECG to Individual Identification" Biometrics: Theory, Applications and Systems, 2008. BTAS 2008. 2nd IEEE International Conference. IEEE, pp. 1-3, (2008).
McLaughlin, N.B., et al., "Comparison of automatic QT measurement techniques in the normal 12 lead electrocardiogram." Heart, vol. 74, No. 1, pp. 84-89, (1995).

\* cited by examiner

LONG QT SYNDROME DIAGNOSIS AND CLASSIFICATION

RELATED APPLICATION

This application claims the benefit of the filing date of Application No. 62/782,738, filed on Dec. 20, 2018, the contents of which are incorporated herein by reference in their entirety.

FIELD

This invention relates to methods for detecting and diagnosing cardiac disease in a subject. More specifically, the invention relates to diagnosing and classifying long QT syndrome in electrocardiogram signals of a subject.

BACKGROUND

Electrocardiogram (ECG) provides valuable information about cardiac electrical activity. A wide range of cardiac diseases can be diagnosed by analyzing ECG and its characteristics. The ECG is composed of different components including a P wave and a QRS complex followed by a T wave, which represent depolarization/repolarization or contraction of different heart chambers (see FIG. 1). Most heart related issues can be diagnosed by analyzing the morphology, amplitude, and duration of these waves and time differences between them [1].

Long QT Syndrome (LQTS) is an arrhythmogenic cardiac disorder, associated with an abnormal ventricular repolarization which results in ventricular arrhythmias. It is clinically characterized by a prolonged QT interval (defined as the time between the start of the Q wave and the end of the T wave) and abnormal T wave morphology [2]. LQTS could result in an abnormally fast heart rhythm called torsades de pointes which is associated with sudden cardiac death.

More than 16 genetic mutations are currently known to be associated with different types of LQTS. However, more than 65% of the population either have a mutation in gene KCNQ1, which is associated with LQTS Type 1 (LQTS1) or KCNH2 which is associated with LQTS Type 2 (LQTS2).

In clinical practice, QT interval is the only standard and universally accepted quantitative measure used for non-invasive diagnosis of LQTS. It is usually measured by an ECG specialist manually, using one of the well-known formulas such as Bazett's formula [3]:

$$QTc \triangleq \frac{QT}{\sqrt{RR}}, \qquad (1)$$

where QT and RR represent the QT and RR intervals, in seconds, and QTc represents the heart-rate-corrected QT interval. If the maximum QTc measured in an ECG is greater than a threshold (450 ms in males and 470 ms in females), it is typically considered as LQTS [4].

However, measuring the QT interval this way is a time-consuming process which is subject to human error. In fact, statistical analysis reveals that only 50% of cardiologists know how to measure it appropriately [5]. This is because a universally accepted mathematical definition of the onset and/or end point of the T wave does not exist, resulting in a high inter- and intra-analyst variability due to subjective nature of the measurements. Moreover, due to the low signal to noise ratio and low amplitude of the T wave, observation of the T wave morphology is a challenging task in most of the cases.

The distribution of QTc for genotype-positive LQTS and genotype-negative normal ECGs in a dataset is depicted in FIG. 2. As seen in this figure, there is a wide range of overlap between QTc in normal and LQTS patients. A similar observation is also reported in [4] for a large dataset of patients over 24 hours of Holter recordings. According to these observations, the QTc of around 25% of genotype-positive LQTS patients is in the normal range [2]. Hence, even if the error in measuring the QTc is ignored, using the QTc as the only feature for diagnosis LQTS leads to a high rate of false positives and/or false negatives.

On the other hand, ECG delineation is a challenging task as the morphology, amplitude, and duration of ECG components are variable. Specifically, due to the low amplitude of the P and T waves and smooth transition at their boundaries, the onset and offset points are very difficult to locate even by human experts. This issue becomes even more complicated in presence of noise and baseline wandering. Furthermore, there is no universally acceptable definition of the locations of onset and offset points of ECG components. These facts make automatic ECG delineation a challenging problem.

SUMMARY

One aspect of the invention relates to a method for detecting long QT syndrome in a subject, comprising: obtaining data corresponding to an electrocardiogram (ECG) signal of the subject; identifying a set of features in the data based on selected inflection points of the ECG signal; using the set of features to categorize segments of the ECG signal; using the categorized segments of the ECG signal and the inflection points to classify the ECG signal as normal or as long QT syndrome; wherein long QT syndrome is detected when the subject's ECG signal is classified as long QT syndrome.

In one embodiment, categorizing segments of the ECG signal includes determining beginning and end points of Q and T waves.

The method may comprise selecting inflection points of the ECG signal by finding zero-crossings of a second derivative of the ECG signal.

In one embodiment, the second derivative of the ECG signal is determined using a finite impulse response (FIR) filter. In one embodiment, the finite impulse response filter comprises a one-dimensional Laplacian of Gaussian (LoG) filter.

In one embodiment, the second derivative of the ECG signal is determined by eliminating variations of ECG signal concavity created by noise and by eliminating the effect of baseline wandering of the ECG signal.

The method may further comprise identifying ECG segments enclosed by two consecutive inflection points and categorizing each ECG segment into a cluster selected from P wave, QRS complex, T wave, and baseline.

In one embodiment, categorizing ECG segments is performed according to a multi-dimensional feature space. In one embodiment, categorizing ECG segments is performed according to a four dimensional feature space. In one embodiment, the four dimensional feature space for an ECG segment comprises duration, energy, maximum distance between amplitude of the ECG segment and a line crossing its boundaries, and standard deviation of a parameter of the ECG segment.

The method may comprise classifying the ECG signal as normal or as LQT syndrome based on two or more features selected from QT interval, base of T wave, rate of T wave fluctuation, slope of T wave at its inflection points, vertical distance between two inflection points at boundaries of the T wave, and heart rate.

The method may comprise using logistic regression on the two or more features to determine a linear boundary between normal and LQT classes.

The method may comprise further classifying a LQT syndrome ECG signal as a LQTS1 ECG signal or a LQTS2 ECG signal.

The method may comprise subjecting the LQT syndrome ECG signal to logistic regression based on a set of features related to T wave morphology.

In one embodiment, the set of features related to T wave morphology comprise number of local peaks, base of the T wave, and difference between the slopes at their boundaries.

Another aspect of the invention relates to a non-transitory computer-readable medium comprising instructions stored thereon, that when executed by a processor, cause the processor to carry out a method as described herein.

In one embodiment, the instructions cause the processor to: receive data corresponding to an electrocardiogram (ECG) signal of a subject; determine inflection points in the ECG signal; identify a set of features in the data based on the inflection points; use the set of features to categorize segments of the ECG signal; use the categorized segments of the ECG signal and the inflection points to classify the ECG signal as normal or as long QT syndrome; output a result indicating whether the subject's ECG signal is classified as long QT syndrome.

In one embodiment, the instructions cause the processor to output a result indicating whether the subject's ECG signal is classified as long QT syndrome Type 1 or long QT syndrome Type 2.

Another aspect of the invention relates to an apparatus, comprising a processor, wherein the apparatus is adapted to: receive data corresponding to an electrocardiogram (ECG) signal of a subject; process the ECG data according to a method as descried herein; and output a result indicating whether or not the subject has long QT syndrome.

BRIEF DESCRIPTION OF THE DRAWINGS

For a greater understanding of the invention, and to show more clearly how it may be carried into effect, embodiments will be described, by way of example, with reference to the accompanying drawings, wherein.

DETAILED DESCRIPTION OF EMBODIMENTS

A variety of approaches have been proposed for automatic QT interval analysis including: threshold-based algorithms [7], [8], hidden Markov models [6], curve fitting [2], wavelet transform [9] and machine learning techniques [10]. In general, such approaches consist of the following main steps: 1) preprocessing, 2) ECG segmentation, 3) QT interval analysis and 4) LQTS classification.

The existing methods suffer from a variety of issues. They are sensitive to low-amplitude T waves, noise, and baseline wandering. Moreover, their accuracy dependents on the threshold levels used for decision making which are mostly adjusted arbitrarily, making most of them semi-automatic algorithms. Furthermore, some of the existing methods require a prior knowledge about the QRS and T waves characteristics, e.g., width and morphology. Pattern recognition methods have also been proposed although they are not accurate in delineating abnormal ECGs. Therefore, a comprehensive automatic approach which is able to deal with different morphologies and amplitude levels of T and QRS waves in noisy ECGs with baseline wandering is highly desirable.

Figure 1:
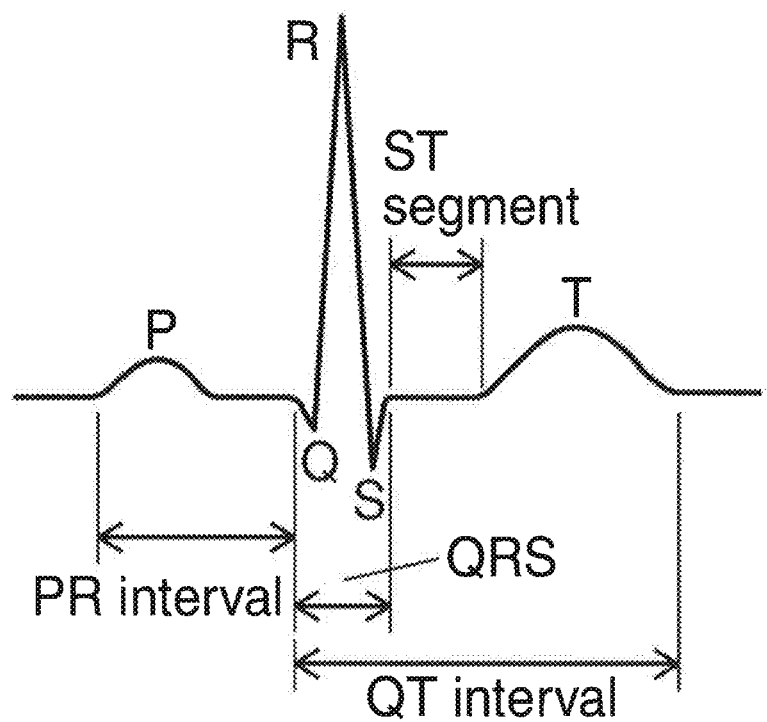
FIG. 1 is a diagram showing components and intervals of a normal ECG waveform.
Figure 2:
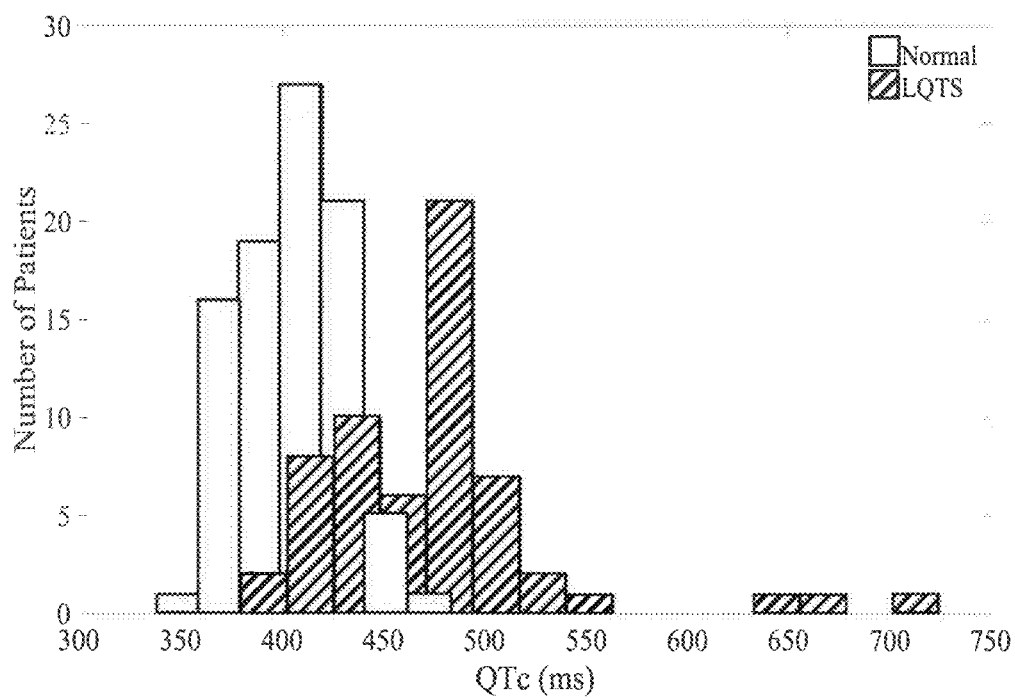
FIG. 2 is a histogram showing distribution of heart-rate-corrected QT interval (QTc) for genotype-positive LQTS, and genotype-negative normal ECGs.
Figure 3:
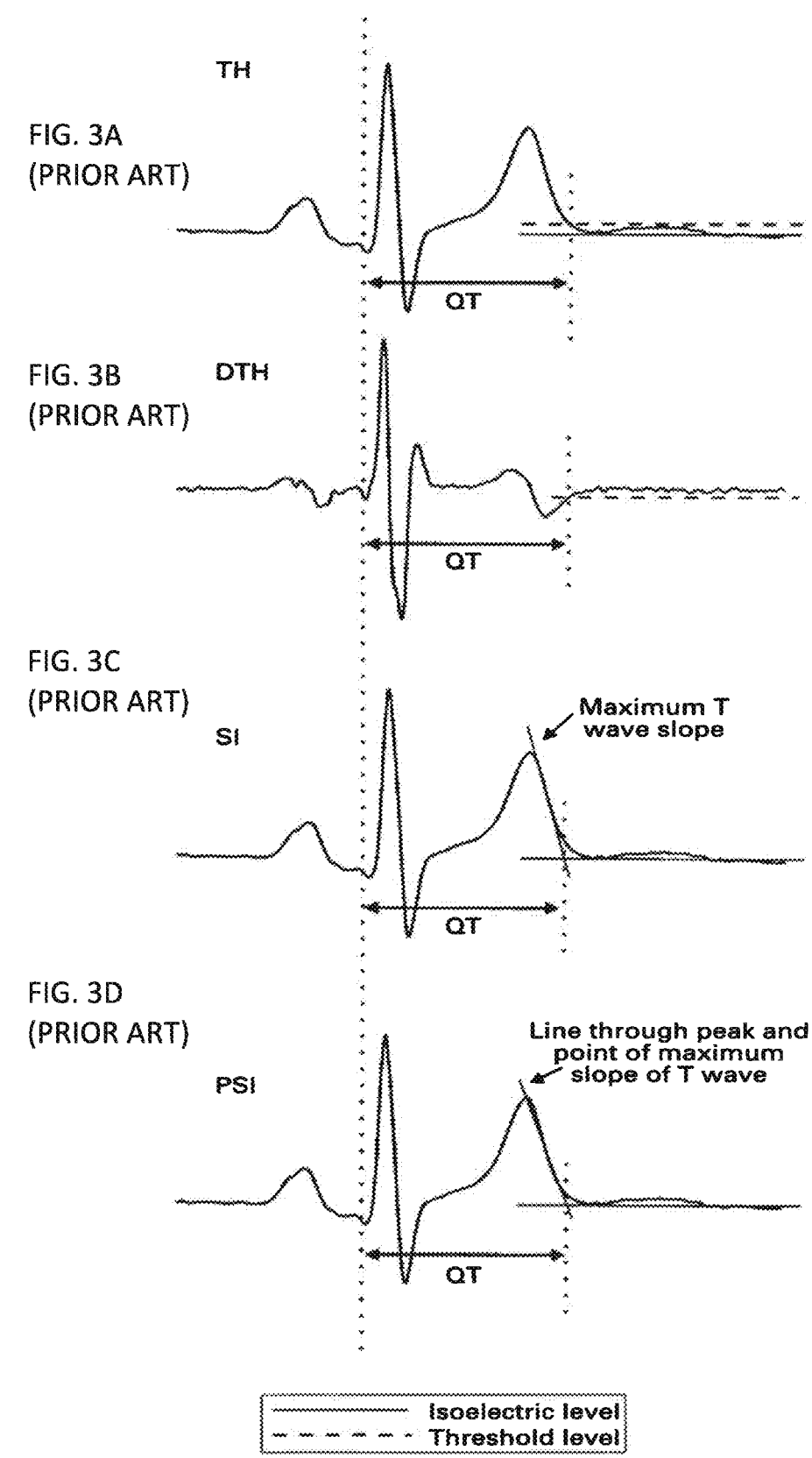
FIGS. 3A-3D are diagrams showing different QT interval measurement methods, including threshold (TH), differential threshold (DTH), slope intercept (SI), and peak slope intercept (PSI), respectively.

FIGS. 3A-3D show various clinical approaches practiced by cardiologists for finding the onset/offset of the QRS complex and the T wave, including amplitude threshold (TH; FIG. 3A), differential threshold (DTH; FIG. 3B), slope intercept (SI; FIG. 3C), and peak slope intercept (PSI: FIG. 3D) [11]. Recent studies show that among these methods, the SI method is the most reliable in clinical practice [12]. In this method, a cardiologist defines the intersection between the maximum negative slope line of the T wave and baseline as the offset of the T wave.

Moreover, existing methods look for the onset and offset of ECG waves. Although it is almost impossible to locate the exact beginning and end points of the P, QRS, and T waves in ECGs, analyzing the characteristics of ECGs at their IPs is more straightforward as they can be described mathematically.

One aspect of the invention relates to a method for automatically diagnosing and classifying different types of long QT syndrome. Embodiments may be implemented in automated systems that diagnose and classify long QT syndrome in patients, and, e.g., are able to identify patients who are at a high risk of mortality. The method includes identifying a set of features of an ECG signal based inflection points (IPs) of the ECG signal. The set of features is then used to characterize and classify the ECG signal as being long QT syndrome or normal, and Type 1 or Type 2 long QT syndrome. The method improves the robustness of ECG segmentation significantly, which in turn provides superior accuracy of diagnosis and classification relative to prior approaches.

Instead of using traditional lowpass/highpass filtering and windowing techniques as in prior approaches, the embodiments employ a Laplacian of Gaussian (LoG) filter for inflection point detection. This results in a significantly higher resolution and lower computational complexity. Furthermore, the method is robust to noise and baseline wandering.

In addition, prior approaches may locate IPs by finding zero-crossings of the second derivative of ECGs. However, since the ECG recordings are corrupted by noise, applying the derivative functions boosts the noise and makes the output signals unstable. Embodiments described herein overcome this problem by using a one-dimensional LoG filter. The LoG is a finite impulse response (FIR) filter which delivers the second derivative of the Gaussian smoothed version of the input signal. The Gaussian part of the LoG filter performs as a low-pass filter which eliminates variations of signal concavity created by noise. On the other hand, the Laplacian part of the filter performs as a high-pass filter which eliminates the effect of baseline wandering.

Figure 4:
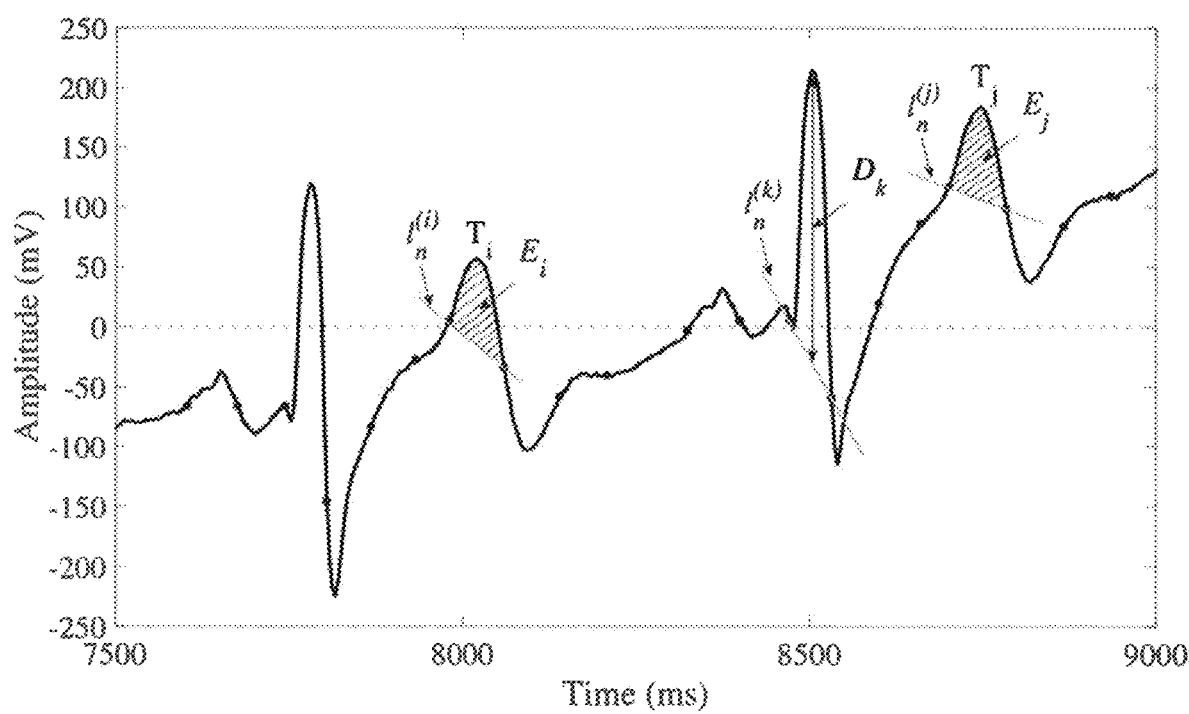
FIG. 4 is a plot showing an ECG signal with baseline wandering, wherein dots represent inflection points extracted using equation (3) presented herein, and shaded areas show the truncated energy determined according to equation (5) presented herein.

The output of LoG filter is then calculated as:

$$y_n = \text{LoG}_n^{(\sigma)} * x_n \quad (2)$$

in which * represents the convolution. The IPs are then identified by locating the zero-crossings of $y_n$:

$$z_m = \{1 \leq n \leq N | y_n \cdot y_{n-1} \leq 0\}, m = 1, \ldots, M, \quad (3)$$

where $z_m$ contains the time indexes of IPs and N and M represent the number of signal samples and IPs, respectively. Once the IPs are located, the ECG segments surrounded by two consecutive IPs are evaluated in order to categorize them into one of four possible clusters: P wave, QRS complex, T wave, and baseline. This is performed using the characteristics of these segments at their IPs. FIG. 4 shows an ECG signal as well as its corresponding IPs.

Various features may be considered for inclusion in a multi-dimensional feature space, which is then subjected to analysis to diagnose and classify different types of long QT syndrome. For example, one or more features may be selected from:

Time distance (duration) between consecutive IPs
Energy of an ECG segment
Distance between the maximum amplitude of an ECG segment and a line crossing its boundaries
Standard deviation of a parameter of one or more of ECG segments
Heart Rate
QTc Bazzet (median & upper adjacent)
QTc Fridericia (median & upper adjacent)
QTc Framingham (median & upper adjacent)
QT/RR (median & upper adjacent)
Number of IPs in T wave (median & upper adjacent)
Base of T wave (median & upper adjacent)
Difference between IPs of T wave (median & upper adjacent)
Difference between slope of IPs of T wave (median & upper adjacent)
Distance between peaks of T and R waves In the embodiment described below, four features were selected for the multi-dimensional space: duration $W_m$, energy $E_m$, distance $D_m$, and standard deviation $S_m$. These are described in detail below. However, it will be appreciated that the invention is not limited thereto, as other features and combinations of features may also be used.

From FIG. 4 it can be seen that a prominent characteristic of an ECG segment is its duration. Therefore, the duration, or time distance between two consecutive IPs, was used as the first feature:

$$W_m \triangleq \frac{|z_m - z_{m-1}|}{f_s}, m = 2, \ldots, M, \quad (4)$$

The second feature used was energy of ECG segments. The energy of an ECG segment may be defined as the sum of squared values of that wave. However, because of baseline wandering, this may not be accurate as low-energy waves positioned at higher baseline values may mistakenly be considered as high-energy segments. Furthermore, isoelectric segments may represent high energy values. These facts can be observed in FIG. 4. For example, as seen in FIG. 4, the isoelectric segment at time 9000 ms has a higher energy than the T wave at time 8000 ms. Therefore, the term "truncated energy" (Em) was defined as the energy concentrated inside each curve of the ECG signal. This energy was measured as the sum of squared distances between the amplitude and the line connecting two IPs at the segment boundaries:

$$E_m \triangleq \frac{f_s}{|z_m - z_{m-1}|} \sum_{n=z_{m-1}}^{z_m} (x_n - l_n^{(m)})^2 \quad (5)$$

In this equation, $l_n^{(m)}$ is a linear function representing the line which crosses two consecutive IPs, defined as follows:

$$l_n^{(m)} \triangleq \frac{x_{z_{m-1}}(z_m - n) + x_{z_m}(n - z_{m-1})}{z_m - z_{m-1}} \quad (6)$$

Note that the multiplication facto $$\frac{f_s}{|z_m - z_{m-1}|}$$

in (5) is the inverse of the ECG segment duration which normalizes the truncated energy for that segment.

In FIG. 4, the truncated energy $E_m$ of two T waves is depicted as shaded areas. As seen in this figure, while the energy of the first T wave ($T_i$) is considerably lower than that of the second T wave ($T_j$), their truncated energy is almost equal ($E_i \approx E_j$). Moreover, the isoelectric segments represent a very low truncated energy while their energy may be high due to baseline variations. This guarantees that ECG waves would fall under the same categories in terms of $E_m$, regardless of baseline wandering.

The maximum distance between the amplitude of an ECG segment and the line crossing its boundaries was used as another feature in the analysis:

$$D_m \triangleq \max |x_n - l_n^{(m)}|, z_{m-1} < n < z_m \quad (7)$$

Where m=[0, 1, 2, . . . , k, . . . , M]]; this distance is shown in FIG. 4 for a typical ECG wave, i.e., $D_k$.

The fourth feature that was used is the standard deviation of the ECG segments:

$$S_m \triangleq \sqrt{\frac{1}{|z_m - z_{m-1}|} \sum_{n=z_{m-1}}^{z_m} |x_n - \mu_m|^2} \quad (8)$$

where:

$$\mu_m = \frac{1}{|z_m - z_{m-1}|} \sum_{n=z_{m-1}}^{z_m} x_n \quad (9)$$

represents the mean of ECG segments. The two previous features are useful for distinguishing between segments with the same energy but different morphologies.

The four features described above create a multi-dimensional feature space, in this case four-dimensional. Other features may be used, and/or other numbers of features may be used to create a multi-dimensional feature space, as noted above.

According to the multi-dimensional feature space, the mth ECG segment between two consecutive IPs is represented by the following feature vector:

$$f_m = [W_m E_m D_m S_m]^T \qquad (10)$$

At the next step of the method, the ECG waves are clustered into the four groups: P, QRS, T and baseline, using their properties in feature space. Note that $E_m$ is the only feature that takes on negative or positive values, depending of the polarity of ECG segments, while the rest of the features only take on non-negative values. Therefore, $E_m$ was normalized in the range of $[-1,1]$ and the rest of the features $W_m$, $D_m$ and $S_m$ were normalized in the range of $[0,1]$ in order to avoid biasing. Furthermore, preliminary analyses showed that ECG waves are more distinguishable in feature space when natural logarithms of features is employed. This is because the natural logarithm compensates for skewing of the features. Interestingly, the analyses also reveal that the natural logarithms of features exhibit a distribution of mixture of four Gaussian components, each for one of the P, QRS and T waves and baseline.

Therefore, an Expectation Maximization (EM) algorithm for Gaussian mixtures was used in order to cluster the feature vectors automatically. Hence, the underlying density was defined as a Gaussian Mixture Model (GMM) with C components:

$$p(f \mid \Theta) = \sum_{i=1}^{C} \tau_i \mathcal{N}(f \mid s_i, \mu_i, \Sigma_i), \qquad (11)$$

where N represents a multivariate Gaussian distribution with mean $\mu_i$ and covariance matrix $\Sigma_i$. The unknown parameter vector $\Theta$ was defined as:

$$\Theta = \{\tau_1, \ldots, \tau_C, \mu_1, \ldots, \mu_C, \Sigma_1, \ldots, \Sigma_C\} \qquad (12)$$

$s = (s_1, \ldots, s_C)$ is also a vector of C binary indicator variables which indicates the cluster to which $f_m$ belongs. Finally, $r_i$ is the probability that $f_m$ belongs to the ith cluster. The EM algorithm updates the parameter vector $\Theta$ using the two steps E and M until the log-likelihood function converges:

$$\log \mathcal{L}(\Theta) = \sum_{m=1}^{M} \log p(f_m \mid \Theta). \qquad (13)$$

Figure 5A:
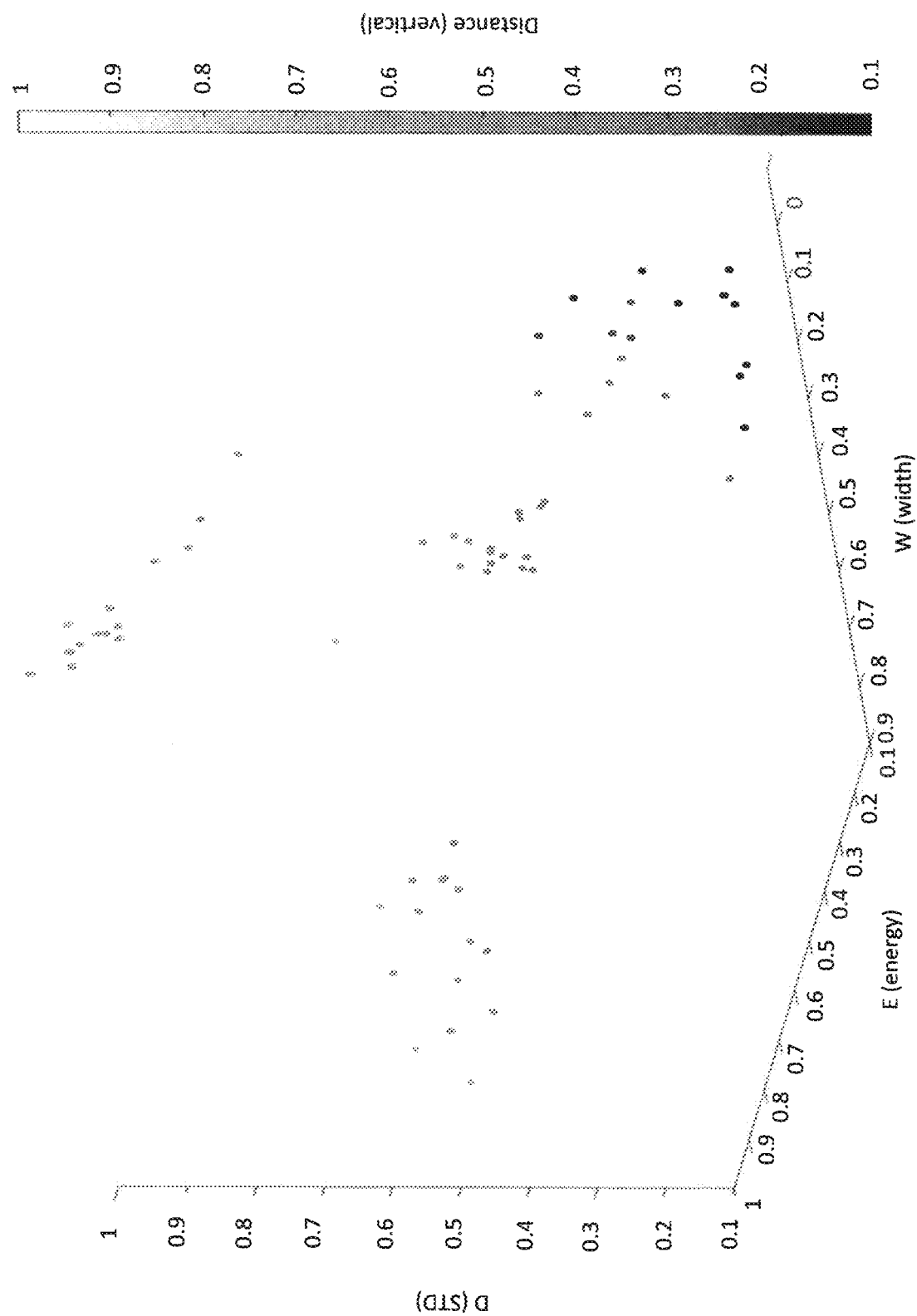
FIGS. 5A and 5B are plots showing segmentation results for a typical ECG in (A) feature space and (B) time domain.
Figure 5B:
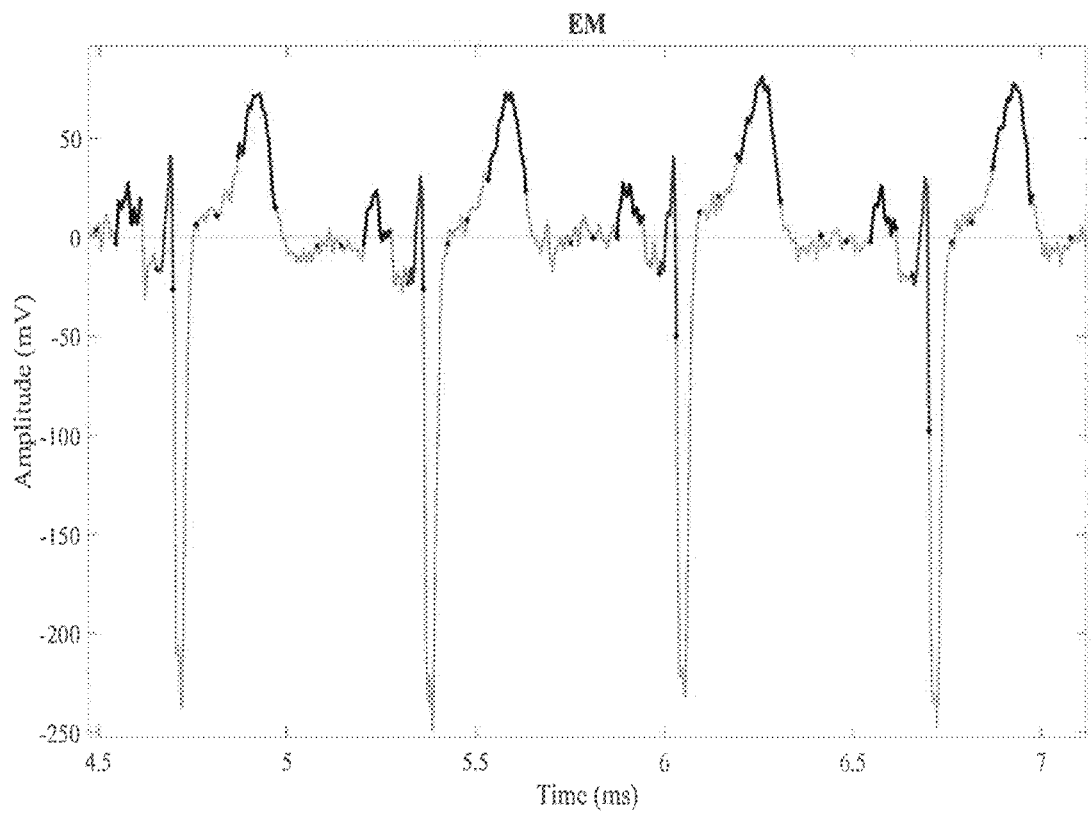

Experimental segmentation results for a typical ECG signal are depicted in FIG. 5A for feature space and in FIG. 5B for the time domain.

QT Interval Measurement and Analysis

Figure 6:
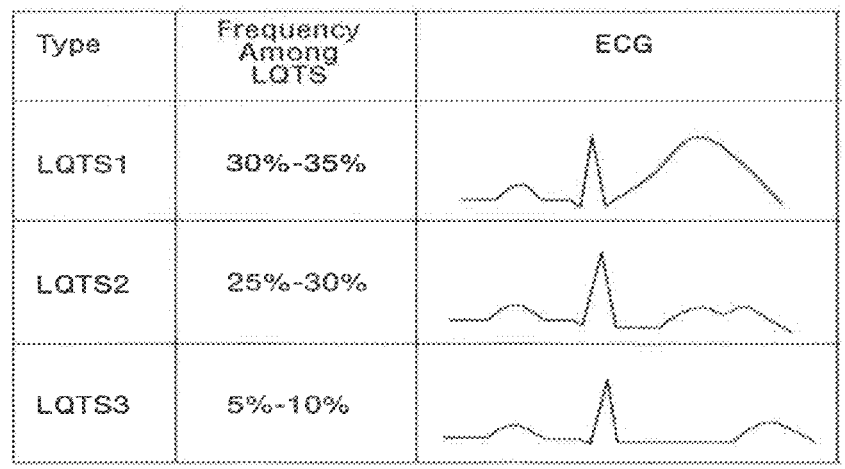
FIG. 6 is a chart showing genotype-phenotype correlation in three types of Long QT Syndromes.

Once the segments of the ECG waves are identified, the QT interval is analyzed in order to classify subjects into one of the three categories: Normal, LQTS Type 1 (LQTS1) and LQTS Type 2 (LQTS2). The T wave morphology of these three types of LQTS is depicted in FIG. 6. As seen in this figure, in patients with LQTS1, the T wave is typically a prolonged wave with a relatively high amplitude and a wide base. However, in most of the cases, no distinct onset and/or end point can be identified for the T wave. On the other hand, in patients with LQTS2, the T wave is usually a delayed wave with a relatively low amplitude and fluctuations on its peak. Although the onset of the T wave is more obvious in this case, locating the end point is still challenging.

Figure 7:
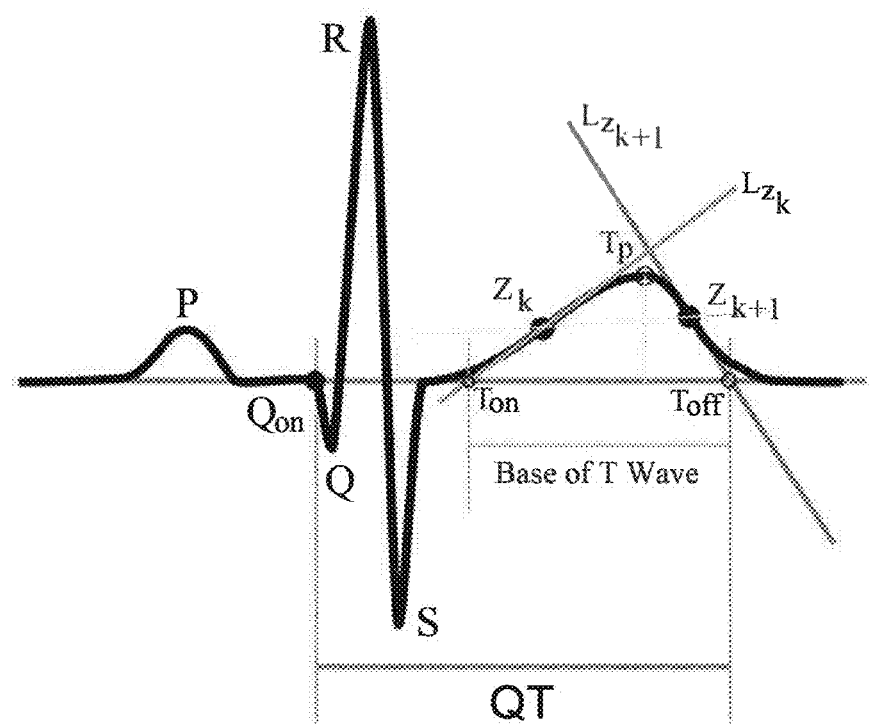
FIG. 7 is a diagram showing inflection points and intervals in an ECG.

To quantify these measures so that they can be employed in an automatic classification technique, a new set of features based on the IPs is set forth herein:

1) QT Interval: The first feature that needs to be measured is the QT interval. As mentioned above, there are multiple clinical approaches for finding the onset/offset of QRS complex and T wave. However, since the SI is the most reliable method in clinical practice, the QT interval is measured using this approach. In this method, the intersection between the maximum negative slope line of the T wave and baseline is defined as the offset of the T wave (FIG. 7). As seen in FIG. 7, first the tangent line passing through the IP $z_{k+1}$ at the end of the T wave ($L_{z_{k+1}}$) is found. However, in order to make it robust to the variations caused by noise, the average of slopes at, e.g., five samples around $z_{k+1}$, i.e., $[z_{k+1}-2:z_{k+1}+2]$ is used. As depicted in FIG. 7, the QT interval is then measured as the time difference between the IP at the onset of the Q wave ($Q_{on}$) and the intersection of $L_{k+1}$ and baseline ($T_{off}$):

$$QT = T_{off} - Q_{on}. \qquad (14)$$

The baseline is also defined as the horizontal line that passes through Q.

2) Base of T wave: The width of the T wave is another feature which is typically measured from beginning to the end of the T wave. However, as seen in FIG. 6, the beginning and end of the T wave are not clear in some cases, especially in patients with LQTS1. Hence, the intersection of a tangent line at the left IP of the T wave ($L_{z_k}$) and the baseline is used as the onset of the T wave ($T_{on}$ in FIG. 7). Therefore, the base of the T wave is defined as: $T_{off}-T_{on}$. The baseline is also defined as the horizontal line that passes through $Q_{on}$. Similar to what was applied to $L_{z_{k+1}}$, the average of slopes at, e.g., five samples around $z_k$, i.e., $[z_k-2:z_k+2]$ is used to make it more robust to the noise.

Figure 8:
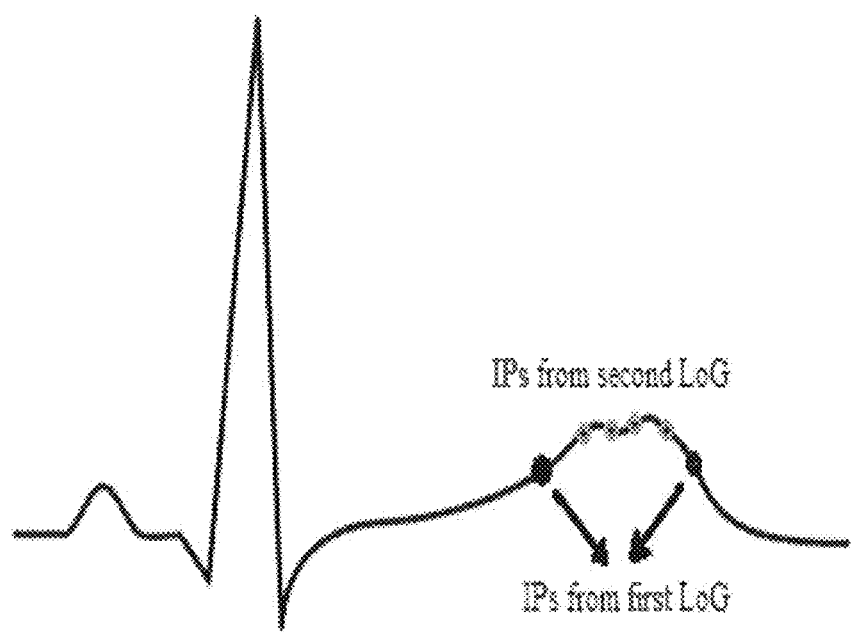
FIG. 8 is a diagram showing inflection points extracted from first (dark dots) and second (gray dots) LoG filters.

3) Rate of T wave Fluctuations: The rate of fluctuations at the peak of the T wave is another feature which is used for distinguishing between LQTS1 and LQTS2. Since the LoG filter applied to the ECG signals is robust to the small fluctuations on the top of the T wave, it cancels them and hence they are not extracted as IPs. However, if another LoG filter with a smaller kernel size (e.g., five samples) is applied to the original signal of the T wave, the noise is reduced but the T wave fluctuations are preserved. Thus, the number of new IPs between the original IPs extracted from the previous LoG filter is used as a new feature. These new IPs are depicted in FIG. 8 as gray dots while the original IPs are depicted as dark dots.

4) Slopes at IPs: The slopes of the T wave at its IPs are used as two new features. These features may be measured as the slopes of lines $L_{z_k}$ and $L_{z_{k+1}}$ in FIG. 7. The rate of the difference between the slopes of these two lines is another morphological feature that represents the symmetry between the left and right half of the T wave:

$$D_{SL}^{(k)} = \frac{|\text{slope}(L_{z_k})| - |\text{slope}(L_{z_{k+1}})|}{|\text{slope}(L_{z_{k+1}})|}, \qquad (15)$$

where |.| represents the absolute value and slope(.) delivers the slope of the lines $L_{z_k}$ and $L_{z_{k+1}}$.

5) Difference Between IPs: The vertical difference between two IPs at the boundaries of the T wave are used as another morphological feature:

$$D_{IP}^{(k)} = x_{z_{k+1}} - x_{z_k}. \qquad (16)$$

6) Heart Rate: The feature of heart rate may be measured as follow:

$$HR = \frac{60}{RR} \quad (17)$$

where RR represents the time interval between two consecutive peaks of the R wave in seconds.

LQTS Diagnosis and Classification

Figure 9:
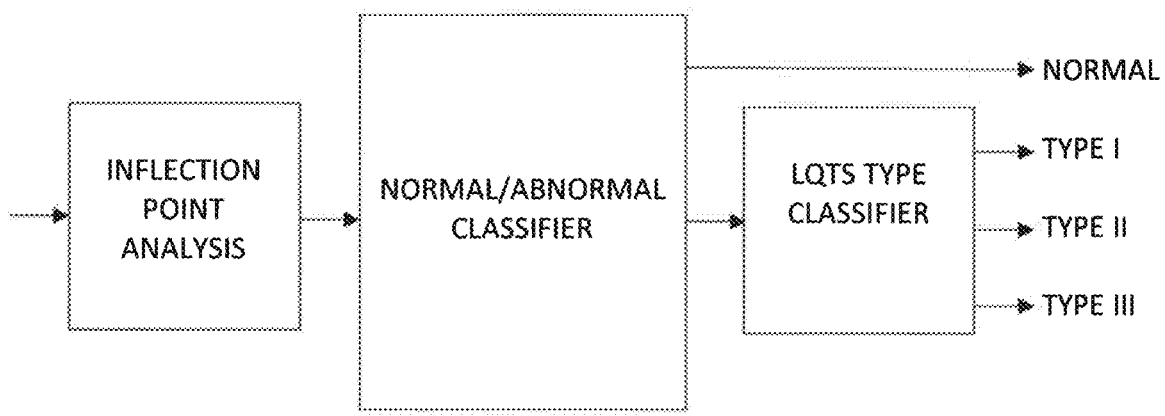
FIG. 9 is a block diagram of a system architecture according to one embodiment.

Diagnosis of LQTS syndrome is a fundamentally important aspect of embodiments. The ability to classify different types of LQTS syndrome is another aspect that is of interest, however, the goal is to identify a potential LQTS patient and refer the patient to the hospital with a high accuracy regardless of the type of LQTS (although it is important to have some information about the type of LQTS). Therefore, in contrast with most of the existing methods in this area, a hierarchical approach is used for diagnosis and classification of LQTS. In the first step, a patient is classified into one of two categories: Normal and LQTS. In the second step, the LQTS patient is classified into one of two groups, LQTS1 and LQTS2. A block diagram of an embodiment of the system is depicted in FIG. 9.

In each step, logistic regression is used for classification, which creates a linear boundary between the different classes. Note that for each ECG signal, the values of the features vary among the heartbeats. Therefore, there is a range of feature values for every patient. In one embodiment, the expected value and variation of the features are considered as two properties, and the mean and standard deviation of the features is used in the calculations. Hence, for every feature introduced in the method there are two values: mean and standard deviation, making the feature space twice as large.

Let $x=[x_1,x_2,x_N]$ be the feature vector. The first logistic regression classifier delivers a vector of weights $\theta=[\theta_0,\theta_1,\theta_N]$ and classifies the ECGs into two classes as follow:

$$LQTS: \text{if } \theta_0 + \sum_{i=1}^{N} \theta_i x_i \geq 0 \quad (18)$$

$$\text{Normal: if } \theta_0 + \sum_{i=1}^{N} \theta_i x_i < 0$$

In the next step, patients with LQTS estimated from the first step are classified into one of two categories: LQTS1 and LQTS2 using another logistic regression classifier. For this purpose, another set of features related to T wave morphology (number of local peaks, base of the T wave, and difference between the slopes at their boundaries) is used. Similar to the first classifier, the second classifier delivers a vector of weights $\beta=[\beta_0,\beta_1,\beta_M]$ and classifies the LQTS patients into one of two classes as follows:

$$LQTS1: \text{if } \beta_0 + \sum_{i=1}^{M} \beta_i x_i \geq 0 \quad (19)$$

$$LQTS2: \text{if } \beta_0 + \sum_{i=1}^{M} \beta_i x_i < 0$$

Embodiments may be implemented using a processor (e.g., a computer, a data processing system, etc.), optionally in conjunction with a graphical user interface (GUI), which may include functions such as receiving input (ECG data, commands from a user of the system, etc.), analyzing data, and displaying results and/or images on a display of the system. For example, the processor may receive and/or process data corresponding to an ECG signal of a subject, and/or perform one or more function as described above, and output a result indicating whether long QT syndrome is detected, and optionally whether the long QT syndrome is Type 1 or Type 2.

The computer includes executable programmed instructions for directing the computer to carry out embodiments of the invention. Executing instructions may include the computer prompting the user for input at various steps. Programmed instructions may be contained in one or more hardware modules or software modules resident in the memory of the computer or elsewhere. Embodiments may include non-transitory programmed media containing instructions. The instructions direct the computer to perform one or more of the functions described above, including, for example, one or more of identifying a set of features in the data based on selected inflection points of the ECG signal; using the set of features to categorize segments of the ECG signal; using the categorized segments of the ECG signal and the inflection points to classify the ECG signal as normal or as long QT syndrome, and optionally to further classify the ECG signal as Type 1 or Type 2 long QT syndrome. The programmed media may direct the computer to output a result indicating whether long QT syndrome is detected when the subject's ECG signal is classified as long QT syndrome, and optionally whether the long QT syndrome is Type 1 or Type 2.

Embodiments will be further described by way of the following non-limiting Example.

Example

Figure 10A:
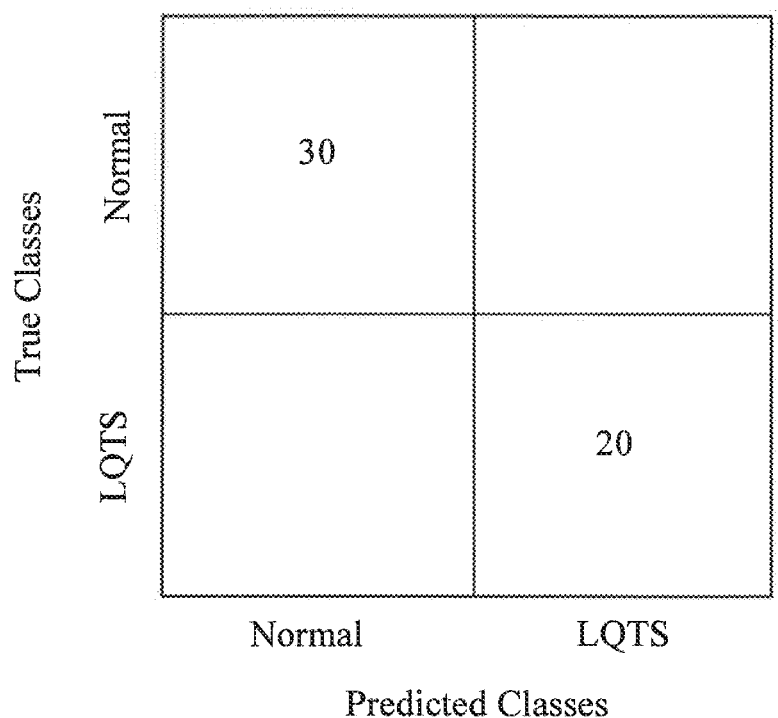
FIGS. 10A and 10B show classification accuracy results for (A) normal/abnormal classifier and (B) LQTS type classifier.
Figure 10B:
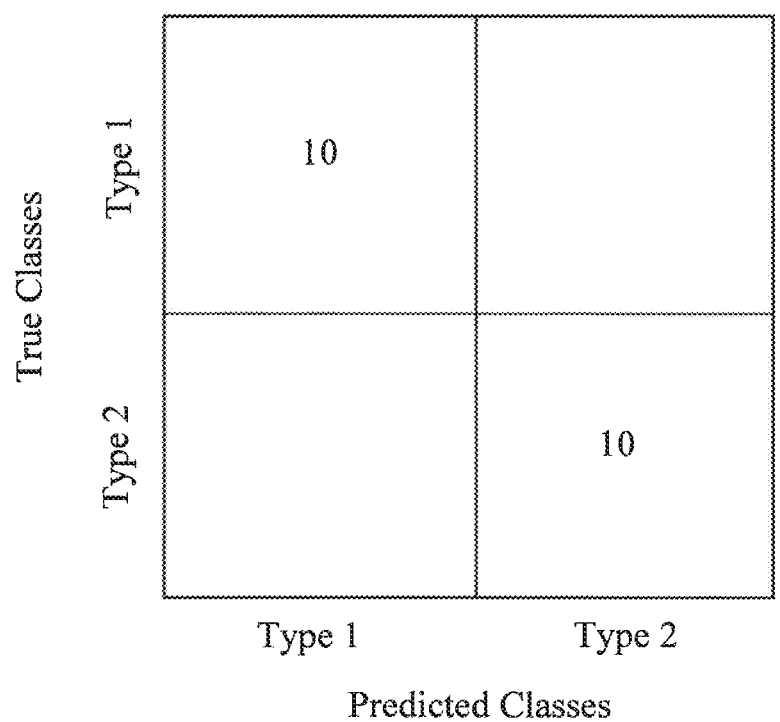

An embodiment as described above was implemented using ECG signals collected from 50 patients, using a standard resting 12-lead ECG. A confusion matrix of the two classifiers is depicted in FIGS. 10A and 10B. The database included ECGs collected from 10 genotype-positive LQTS1 patients, 10 genotype-positive LQTS2 patients, and 30 genotype-negative normal controls. For every patient, 10 seconds of 12-lead ECG signals at a sampling rate of 250 Hz were recorded. A genetic screening result for all patients was also available which was used as a gold standard to confirm the results.

As shown in FIG. 10A, the first step of the method classified the ECGs into normal and LQTS classes with 100% accuracy. Then, in the second step, the LQTS signals were further classified into Type 1 and Type 2 with 100% accuracy as shown in FIG. 10B. Since the method used logistic regression which creates a linear boundary, the method is robust to the problem of over-fitting.

All cited publications are incorporated herein by reference in their entirety.

Equivalents

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

REFERENCES

[1] J. R. Hampton, The ECG Made Easy E-Book. Elsevier Health Sciences, 2013.

[2] S. Immanuel, A. Sadrieh, M. Baumert, J.-P. Couderc, W. Zareba, A. P. Hill, and J. I. Vandenberg, "T-wave morphology can distinguish healthy controls from LQTS patients" Physiological Measurement, vol. 37, no. 9, p. 1456, 2016.

[3] N. P. Hughes, L. Tarassenko, and S. J. Roberts, "Markov models for automated ECG interval analysis" in Advances in Neural Information Processing Systems, 2004, pp. 611-618.

[4] J. P. Martinez and S. Olmos, "Methodological principles of T-wave alternate analysis: a unified framework," IEEE Transactions on Biomedical Engineering, vol. 52, no. 4, pp. 599-613, 2005.

[5] R. Jane, A. Blasi, J. Garc'ia, and P. Laguna, "Evaluation of an automatic threshold based detector of waveform limits in holter ECG with the QT database" in Computers in Cardiology IEEE, pp. 295-298, 1997.

[6] J. J. Struijk, J. K. Kanters, M. P. Andersen, T. Hardahl, C. Graff, M. Christiansen, and E. Toft, "Classification of the long-QT syndrome based on discriminant analysis of T-wave morphology" Medical and Biological Engineering and Computing, vol. 44, no. 7, pp. 543-549, 2006.

[7] L. Marsanova, M. Ronzhina, R. Smisek, M. Vitek, A. Nemcova, L. Smital, and M. Novakova, "ECG features and methods for automatic classification of ventricular premature and ischemic heartbeats: A comprehensive experimental study" Scientific Reports, vol. 7, no. 1, p. 11239, 2017.

[8] J. R. Thorpe, T. Saida, J. Mehlsen, A.-B. Mehlsen, H. Langberg, K. Hoppe, and H. B. Sorensen, "Comparative study of T-amplitude features for fitness monitoring using the epatch R ECG recorder" in Engineering in Medicine and Biology Society (EMBC), 36th Annual International Conference of the IEEE, pp. 4172-4175, 2014.

[9] A. Goutas, Y. Ferdi, J.-P. Herbeuval, M. Boudraa, and B. Boucheham, "Digital fractional order differentiation-based algorithm for P and T waves detection and delineation" ITBM-RBM, vol. 26, no. 2, pp. 127-132, 2005.

[10] Y. N. Singh and P. Gupta, "ECG to individual identification" in Biometrics: Theory, Applications and Systems, 2008. BTAS 2008. 2nd IEEE International Conference. IEEE, 2008, pp. 1-8.

[11] N. B. McLaughlin, R. Campbell, and A. Murray, "Comparison of automatic qt measurement techniques in the normal 12 lead electrocardiogram." Heart, vol. 74, no. 1, pp. 84-89, 1995.

[12] K. Waddell-Smith, R. M. Gow, and Jonathan R. Skinner, "How to measure a QT interval". Medical Journal of Australia, vol. 207 (3), pp. 107-110, 2017.

The invention claimed is:

1. A method for detecting long QT syndrome (LQTS) in a subject, comprising:
obtaining data corresponding to an electrocardiogram (ECG) signal of the subject;
identifying a set of features in the data based on selecting inflection points of the ECG signal by finding zero-crossings of a second derivative of the ECG signal, wherein the second derivative is determined using a finite impulse response (FIR) filter;
using the set of features to categorize segments of the ECG signal;
using the categorized segments of the ECG signal and the inflection points to classify the ECG signal as normal or as long QT syndrome;
wherein long QT syndrome is detected when the subject's ECG signal is classified as long QT syndrome.

2. The method of claim 1, wherein categorizing segments of the ECG signal includes determining beginning and end points of Q and T waves.

3. The method of claim 1, wherein the finite impulse response filter comprises a one-dimensional Laplacian of Gaussian (LoG) filter.

4. The method of claim 1, wherein the second derivative of the ECG signal is determined by eliminating variations of ECG signal concavity created by noise and by eliminating the effect of baseline wandering of the ECG signal.

5. The method of claim 1, further comprising identifying ECG segments enclosed by two consecutive inflection points and categorizing each ECG segment into a cluster selected from P wave, QRS complex, T wave, and baseline.

6. The method of claim 5, wherein categorizing ECG segments is performed according to a multi-dimensional feature space.

7. The method of claim 5, wherein categorizing ECG segments is performed according to a four dimensional feature space.

8. The method of claim 7, wherein the four dimensional feature space for an ECG segment comprises duration, energy, maximum distance between amplitude of the ECG segment and a line crossing its boundaries, and standard deviation of a parameter of the ECG segment.

9. The method of claim 1, comprising classifying the ECG signal as normal or as LQTS based on two or more features selected from QT interval, base of T wave, rate of T wave fluctuation, slope of T wave at its inflection points, vertical distance between two inflection points at boundaries of the T wave, and heart rate.

10. The method of claim 9, comprising using logistic regression on the two or more features to determine a linear boundary between normal and LQTS classes.

11. The method of claim 9, comprising further classifying a LQTS ECG signal as a LQTS Type 1 ECG signal or a LQTS Type 2 ECG signal.

12. The method of claim 11, comprising subjecting the LQTS ECG signal to logistic regression based on a set of features related to T wave morphology.

13. The method of claim 12, wherein the set of features related to T wave morphology comprise number of local peaks, base of the T wave, and difference between the slopes at their boundaries.

14. A non-transitory computer-readable medium comprising instructions stored thereon, that when executed by a processor, cause the processor to carry out processing steps comprising:
receive data corresponding to an electrocardiogram (ECG) signal of a subject;
identify a set of features in the data based on selecting inflection points of the ECG signal by finding zero-crossings of a second derivative of the ECG signal, wherein the second derivative is determined using a finite impulse response (FIR) filter;
use the set of features to categorize segments of the ECG signal;
use the categorized segments of the ECG signal and the inflection points to classify the ECG signal as normal or as long QT syndrome;
output a result indicating whether the subject's ECG signal is classified as long QT syndrome (LQTS).

15. The non-transitory computer-readable medium of claim 14, wherein the instructions cause the processor to output a result indicating whether the subject's ECG signal is classified as LQTS Type 1 or LQTS Type 2.

16. Apparatus, comprising a processor and a non-transitory computer-readable medium having instructions stored thereon, wherein the instructions cause the processor to:
    receive data corresponding to an electrocardiogram (ECG) signal of a subject;
    identify a set of features in the data based on selecting inflection points of the ECG signal by finding zero-crossings of a second derivative of the ECG signal, wherein the second derivative is determined using a finite impulse response (FIR) filter;
    use the set of features to categorize segments of the ECG signal;
    use the categorized segments of the ECG signal and the inflection points to classify the ECG signal as normal or as long QT syndrome (LQTS);
    output a result indicating whether the subject's ECG signal is classified as normal or as long QT syndrome.

17. The apparatus of claim 16, wherein the instructions cause the processor to output a result indicating whether the subject's ECG signal is classified as LQTS Type 1 or LQTS Type 2.

\* \* \* \* \*